US00PP19947P2

(12) United States Plant Patent
Ghyselen

(10) Patent No.: US PP19,947 P2
(45) Date of Patent: Apr. 21, 2009

(54) *BRUNNERA* PLANT NAMED 'MR. MORSE'

(50) Latin Name: *Brunnera macrophylla*
Varietal Denomination: Mr. Morse

(76) Inventor: Chris Ghyselen, Tinhoutstraat 36, Beemem (BE)

( * ) Notice: Subject to any disclaimer, the term of this patent is extended or adjusted under 35 U.S.C. 154(b) by 0 days.

(21) Appl. No.: 11/983,100

(22) Filed: Nov. 7, 2007

(51) Int. Cl.
*A01H 5/00* (2006.01)

(52) U.S. Cl. ..... Plt./412
(58) Field of Classification Search ..... Plt./412
See application file for complete search history.

(56) References Cited

PUBLICATIONS

Walters Gardens. Brunnera Mr. Morse. Available at: http://www.waletrsgardens.com/index.cfm?fuseaction=plants.plantDetail&plant_id1616&printLayout=1.*

* cited by examiner

*Primary Examiner*—Wendy C. Haas
(74) *Attorney, Agent, or Firm*—Penny J. Aguirre

(57) ABSTRACT

A new cultivar of *Brunnera macrophylla,* 'Mr. Morse', characterized by its deep green foliage that heavily mottled with silver with its contrasting green margins and veins combined with panicles of white flowers that are present in mid to late spring.

3 Drawing Sheets

Botanical classification: *Brunnera macrophylla.*
Cultivar designation: 'Mr. Morse'.

BACKGROUND OF THE INVENTION

The present invention relates to a new and distinct cultivar of *Brunnera macrophylla,* and is hereinafter referred to by the cultivar name 'Mr. Morse'.

The inventor discovered the new cultivar, 'Mr. Morse', as a naturally whole plant mutation *Brunnera macrophylla* in a cultivated nursery bed in Beernem, Belgium in 2006. The parent plants of 'Mr. Morse' are unknown, however *Brunnera macrophylla* 'Betty Bowring' (not patented) and *Brunnera macrophylla* 'Inspector Morse' (not patented) are probable parents based on characteristics and presence in the growing area.

Asexual reproduction of the new cultivar was first accomplished under direction of the inventor by in vitro propagation in Rijswijk, The Netherlands in fall of 2006. Asexual reproduction of the new cultivar has shown that the unique features of 'Mr. Morse' are stable and reproduced true to type in successive generations.

SUMMARY OF THE INVENTION

The following traits have been repeatedly observed and represent the characteristics of the new cultivar. These attributes in combination distinguish 'Mr. Morse' as a new and unique cultivar of *Brunnera.*

1. 'Mr. Morse' exhibits foliage with an upper leaf surface that is green with a silvery overlay between the veins and green margins.
2. 'Mr. Morse' exhibits panicles of white flowers in mid to late spring.

'Mr. Morse' is a unique *Brunnera* in combining silver mottled leaves with white flowers. In comparison to its probable parent plants; 'Betty Bowring' has green, non-mottled leaves combined with white flowers and 'Inspector Morse' has silver mottled foliage but exhibits light blue flowers. There are several existing cultivars of *Brunnera* known to the inventor that have leaves with silver mottling in addition to 'Inspector Morse', however all of these cultivars exhibits light blue flowers whereas 'Mr. Morse' exhibits white flowers. These cultivars include; 'Jack Frost' (U.S. Pat. No. 13,859), 'Silver Wings' (U.S. Plant Pat. No. 13,706) and 'Looking Glass' (U.S. Pat. No. 17,829).

BRIEF DESCRIPTION OF THE DRAWING

The accompanying colored photographs illustrate the overall appearance and distinct characteristics of the new *Brunnera.*

The photographs on the first and second sheet were taken in The Netherlands of a six month-old plant as grown outdoors in a one gallon container (the dark areas are due to soil on leaves).

The photograph on the first sheet provides a side view of new cultivar and the photograph in the second sheet is a close-up view of the upper leaf surface of 'Mr. Morse'.

The photograph on the third sheet was taken of a plant one year in age as grown outdoors in a one gallon container in The Netherlands and provides a close-up view of the flowers of 'Mr. Morse'.

The colors in the photographs are as close as possible with the photographic and printing technology utilized. The color values cited in the detailed botanical description accurately describe the colors of the new *Brunnera.*

DETAILED BOTANICAL DESCRIPTION OF THE PLANT

The following is a detailed description of six month and one year-old plants of the new cultivar as grown outdoors in field plots and containers in The Netherlands. The phenotype of the new cultivar may vary with variations in environmental, climatic, and cultural conditions, as it has not been tested under all possible environmental conditions. The color determination is in accordance with the 2001 R.H.S. Colour Chart of the Royal Horticultural Society, London, England, except where general color terms of ordinary dictionary significance are used.

General description:

*Blooming habit.*—Blooms from mid to late spring in The Netherlands.

*Plant habit.*—Clump-forming herbaceous perennial, open mound with flowering stems emerging from basal rosette of foliage.

*Height and spread.*—Reaches about 25 cm in height and about 35 cm in width.

*Cold hardiness.*—U.S.D.A. Zone 3.

*Culture.*—Performs best in medium shade in moist, well-drained, fertile soils.

*Diseases and Pests.*—No more susceptibility or resistance to diseases than other cultivars of *Brunnera*.

*Root description.*—Fibrous roots on woody rootstalks.

*Branching habit.*—Basal rosettes.

*Propagation.*—In vitro propagation is the preferred method.

*Cropping time.*—Average of 20 weeks to finish in the field or in a 9 cm container when grown outdoors under ambient light in The Netherlands.

*Growth rate.*—Moderately vigorous.

Foliage description:

*Leaf shape.*—Reniform.

*Leaf division.*—Simple.

*Leaf base.*—Deeply cordate.

*Leaf apex.*—Acute to cuspidate.

*Leaf venation.*—Laciniate, conspicuous, color on mature leaves; 143A, 144A or 144B on upper surface, color on lower surface 144A.

*Leaf margins.*—Entire with stiff hairs.

*Leaf attachment.*—Petiolate.

*Leaf arrangement.*—Basal rosettes.

*Leaf orientation.*—Held nearly horizontal to petiole, leaf plane is flat to convex with edges occasionally curving downward.

*Leaf surface.*—Upper and lower surface are pubescent, dull, and rough to touch, both surfaces and margin are densely covered with short white (155C) strigose hairs that average 1 mm in length on upper surface and 0.5 mm on lower surface and margin.

*Leaf color.*—Young leaves upper surface; 191B to 191C, young leaves lower surface; 137C to 138A, mature leaves upper surface; 137A heavily mottled with 190C to 190D, mature leaves lower surface; 137C to 138A.

*Leaf size.*—Mature to average of 11.6 cm in length and 12.2 cm width.

*Leaf quantity.*—Average of 19 per one year-old plant.

*Petioles.*—Average of 12 cm in length and 3 mm in width, 144A in color, shape is round becoming sulcate near apex, surface is dull and pubescent with short stiff fine hairs.

Flower description:

*Inflorescence type.*—Terminal paniculate cymes of rotate flowers on leafy flowering stems that arise from base with smaller panicles from upper nodes.

*Flowering stems.*—Average of 25 cm in length and 3 mm in width, color is 138B, surface is pubescent with hairs 155B in color and 0.5 mm in length, cauline leaves; average of 3, spatulate in shape, sessile, average of 8 cm in length and 7.5 cm in width, acute apex, cuneate base, color, venation and surface match basal leaves.

*Inflorescence size.*—Average of 15 cm in height and about 7 cm in width.

*Flower fragrance.*—None detected.

*Flower quantity.*—Average of 4 flowering stems per one gallon sized plant, average of 100 flowers per flowering stem.

*Flower lastingness.*—Average of 7 days per flower, individual panicles blooms for about 3 weeks.

*Flower buds.*—Globose in shape, average of 2.5 mm in diameter and depth, calyx portion is 137D with apex 155B.

*Flower aspect.*—Held horizontal to pedicles held at about a 45° angle from peduncle.

*Flower size.*—Average of 7 mm in diameter and 5 mm in depth.

*Petals.*—5, broadly oblanceolate in shape, fused at base, margin is entire, apex is acute, upper and lower surface is glabrous, color of upper and lower surface is 155B (whiter) with raised ring at center of flower 155B, about 3 mm in length and width.

*Calyx.*—Campanulate with sepals fused at base, about 3.5 mm in width and 1.5 mm in length.

*Sepals.*—5, lanceolate in shape, about 1.5 mm in length and 0.4 mm width, margin is entire, apex is acute, base is fused, surface pubescent, color of upper and lower surface is 138A.

*Peduncles.*—Average of 2 cm in length and 1.5 mm in width on individual cymes, pubescent surface, color 138B.

*Pedicels.*—Average of 5 mm in length and about 1 mm in width, pubescent surface, color 137B.

Reproductive organs:

*Gynoecium.*—Pistil, about 4 mm in length and <0.3 mm in width, stigma about 0.25 mm in width and length, ovary superior and about 0.5 mm in diameter and height, style, stigma, and ovary 155B in color.

*Androcoecium.*—5 stamens, included, basifixed, about 2.5 mm in length and 10.7 mm in width and 155B in color, anthers about 0.5 mm in length and 187A in color, pollen 158D in color.

*Seed.*—Nutlet, about 0.7 mm in diameter, 200A in color.

It is claimed:

1. A new and distinct cultivar of *Brunnera* plant named 'Mr. Morse' as herein illustrated and described.

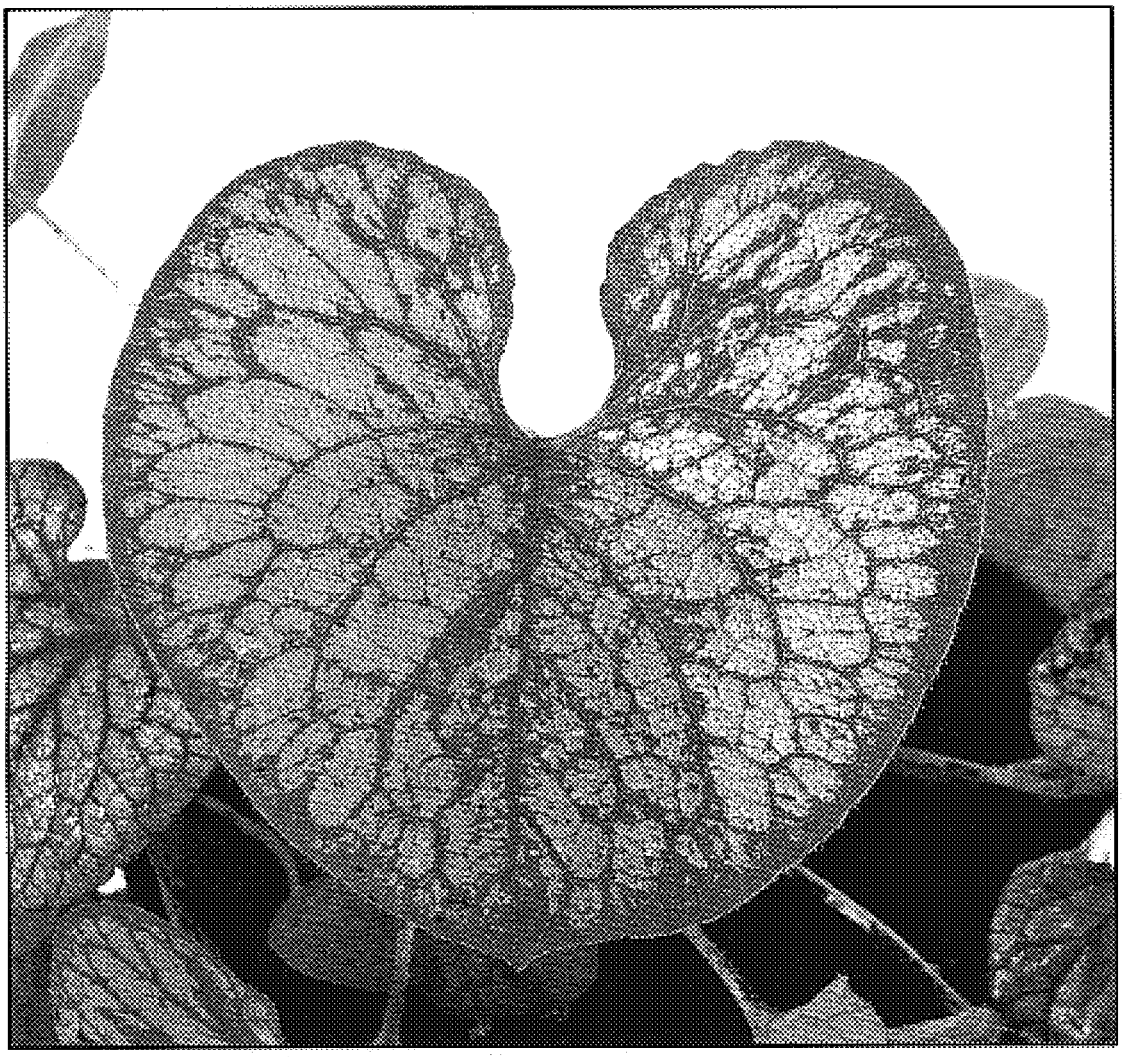

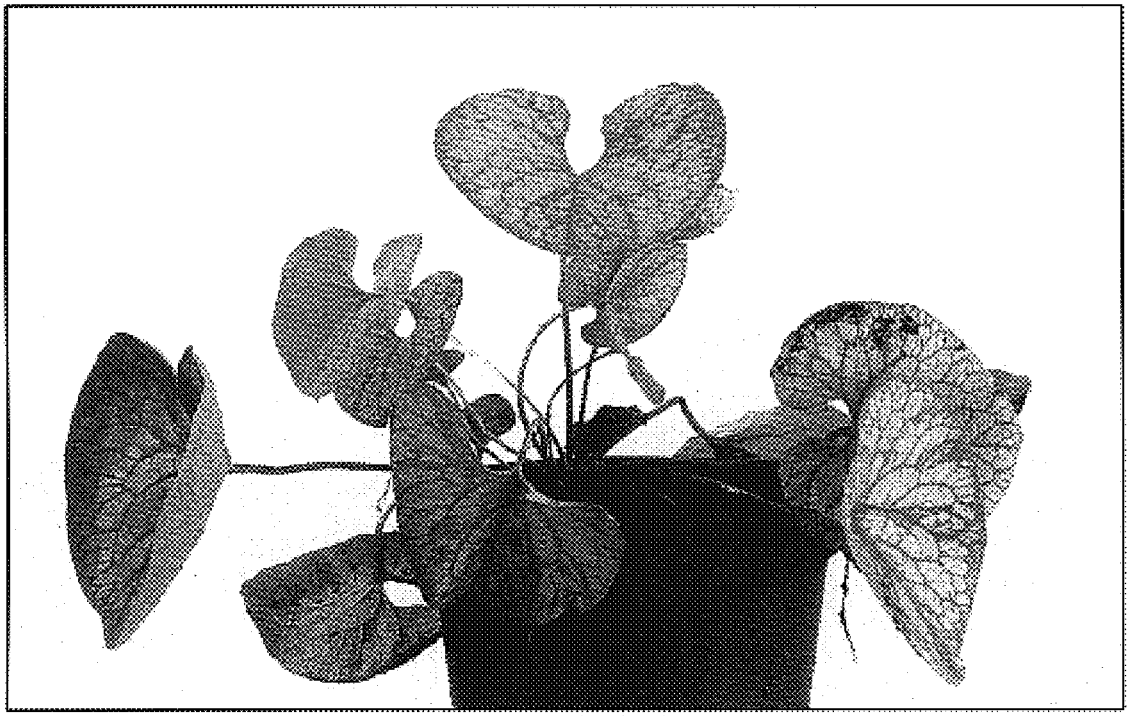

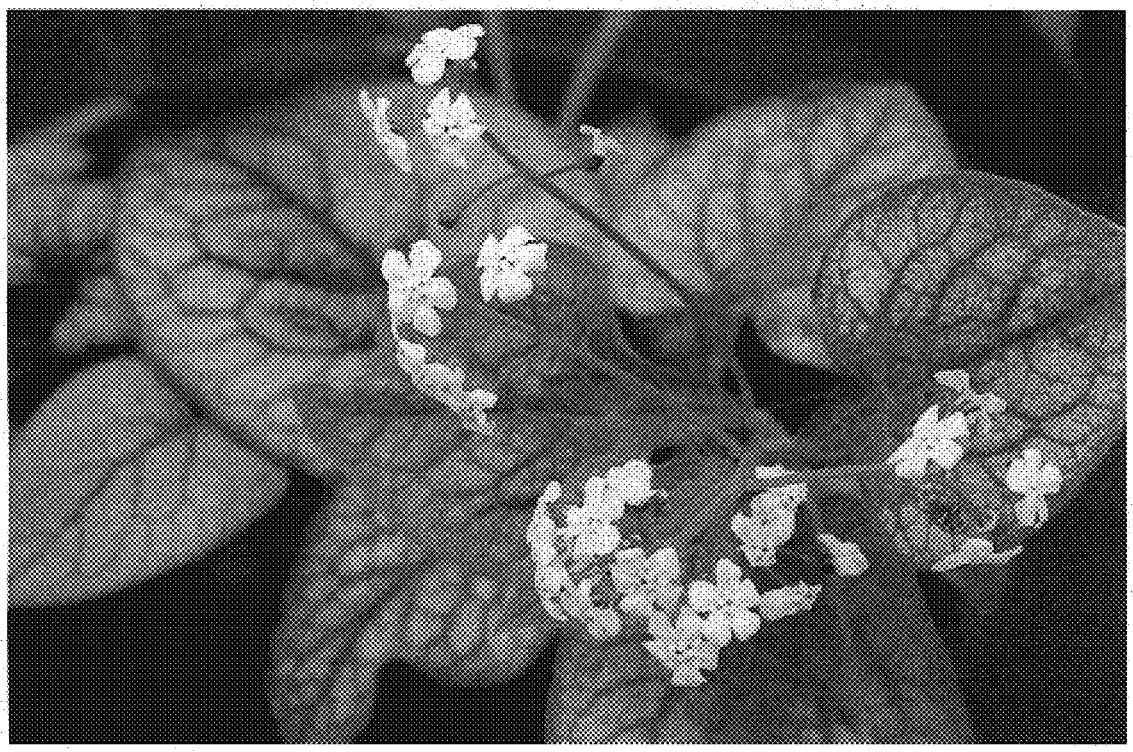

* * * * *